United States Patent [19]
Greensides

[11] 3,931,680
[45] Jan. 13, 1976

[54] FOOT MEASURING MACHINES

[75] Inventor: Christopher John Greensides, Waltham on the Wolds, near Melton Mowbray, England

[73] Assignee: Clarks Limited, Somerset, England

[22] Filed: Jan. 23, 1974

[21] Appl. No.: 435,946

[52] U.S. Cl. .................................................. 33/3 B
[51] Int. Cl.² .............................................. A43D 1/00
[58] Field of Search ............... 33/3 R, 3 A, 3 B, 3 C

[56] References Cited
UNITED STATES PATENTS

| | | | |
|---|---|---|---|
| 973,475 | 10/1910 | Church | 33/3 C |
| 1,167,269 | 1/1916 | Church | 33/3 C |
| 2,657,463 | 11/1953 | Spencer | 33/3 R |
| 3,032,880 | 5/1962 | Shaw | 33/3 C |
| 3,328,882 | 7/1967 | Blivice | 33/3 C |
| 3,494,036 | 2/1970 | Stiebel et al. | 33/3 C |
| 3,173,208 | 3/1965 | Dana | 33/3 A |

*Primary Examiner*—William D. Martin, Jr.
*Assistant Examiner*—Charles E. Phillips
*Attorney, Agent, or Firm*—Burgess Ryan and Wayne

[57] ABSTRACT

The specification describes an automatic machine for measuring the length, width and girth of a foot for the purpose of determining the most appropriate shoe size. The machine measures the width of the foot at a distance approximately three quarters of the length of the foot from the heel end and measures the girth of the foot at the same position. Placing the heel against a heel stop on a platform initiates motor driven movement of a toe stop towards the toes. When the toe stop comes into abutment with the toes, a microswitch is actuated which starts a motor driving one of two width probes for bringing the two width probes into engagement with opposite sides of the foot, the width probes being coupled together for lateral floating movement. The width probes are mounted on a carriage which is driven lengthwise of the foot in conjunction with the toe stop end at three-quarters of the speed of the toe stop. Contact of the width probes with opposite sides of the foot actuates motors which cause two girth probes mounted on the said carriage to move towards each other laying tape across the instep of the foot. When the girth probes touch each other, their relative movement towards each other is terminated. Motors which respectively drive the toe stop, width probes and girth probes are connected to respective pointers which provide measures of the length, width and girth of the foot.

14 Claims, 11 Drawing Figures

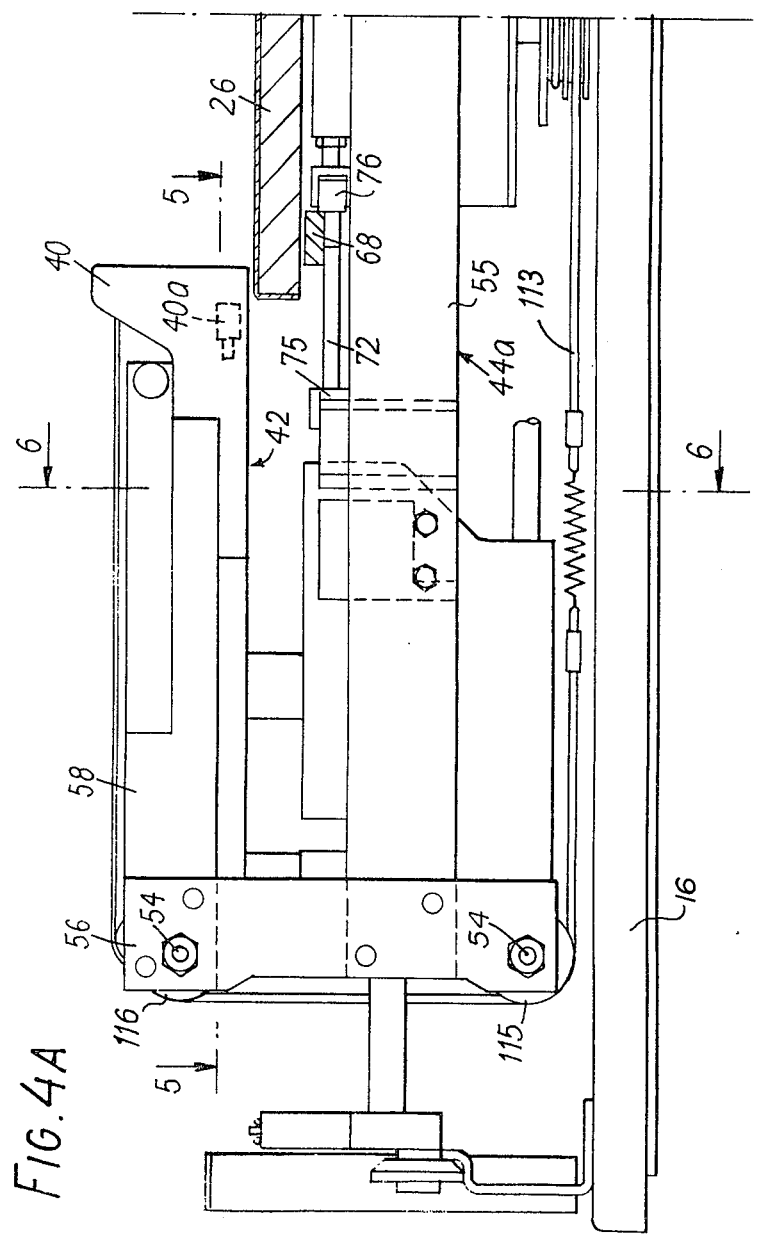

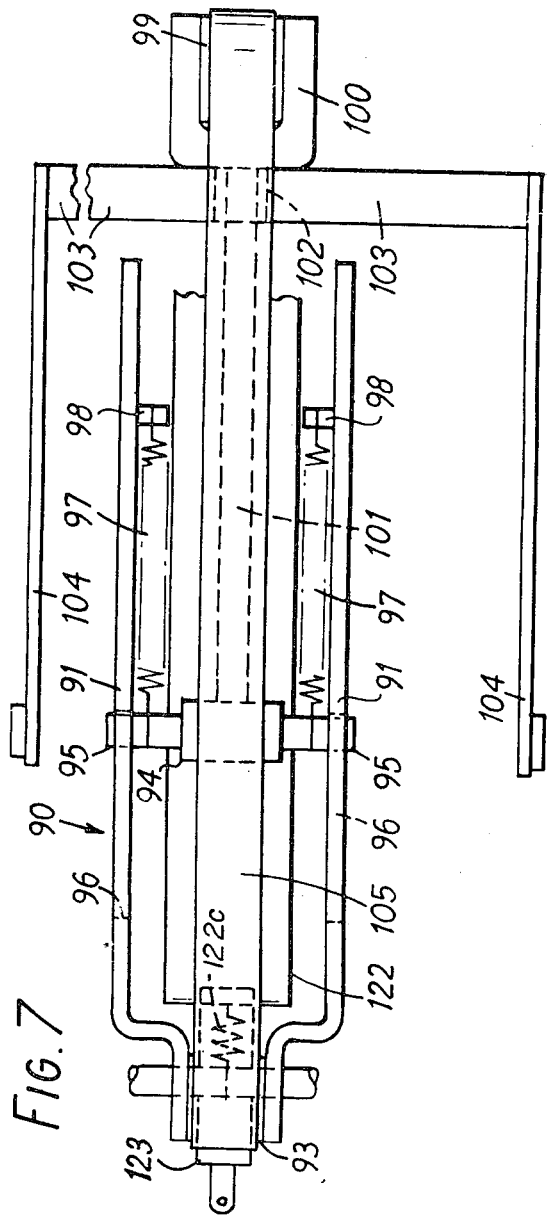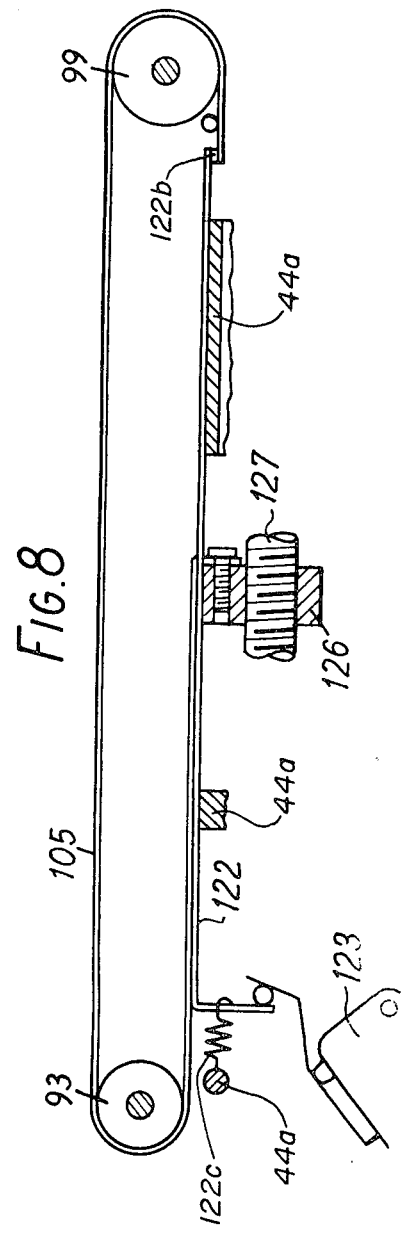

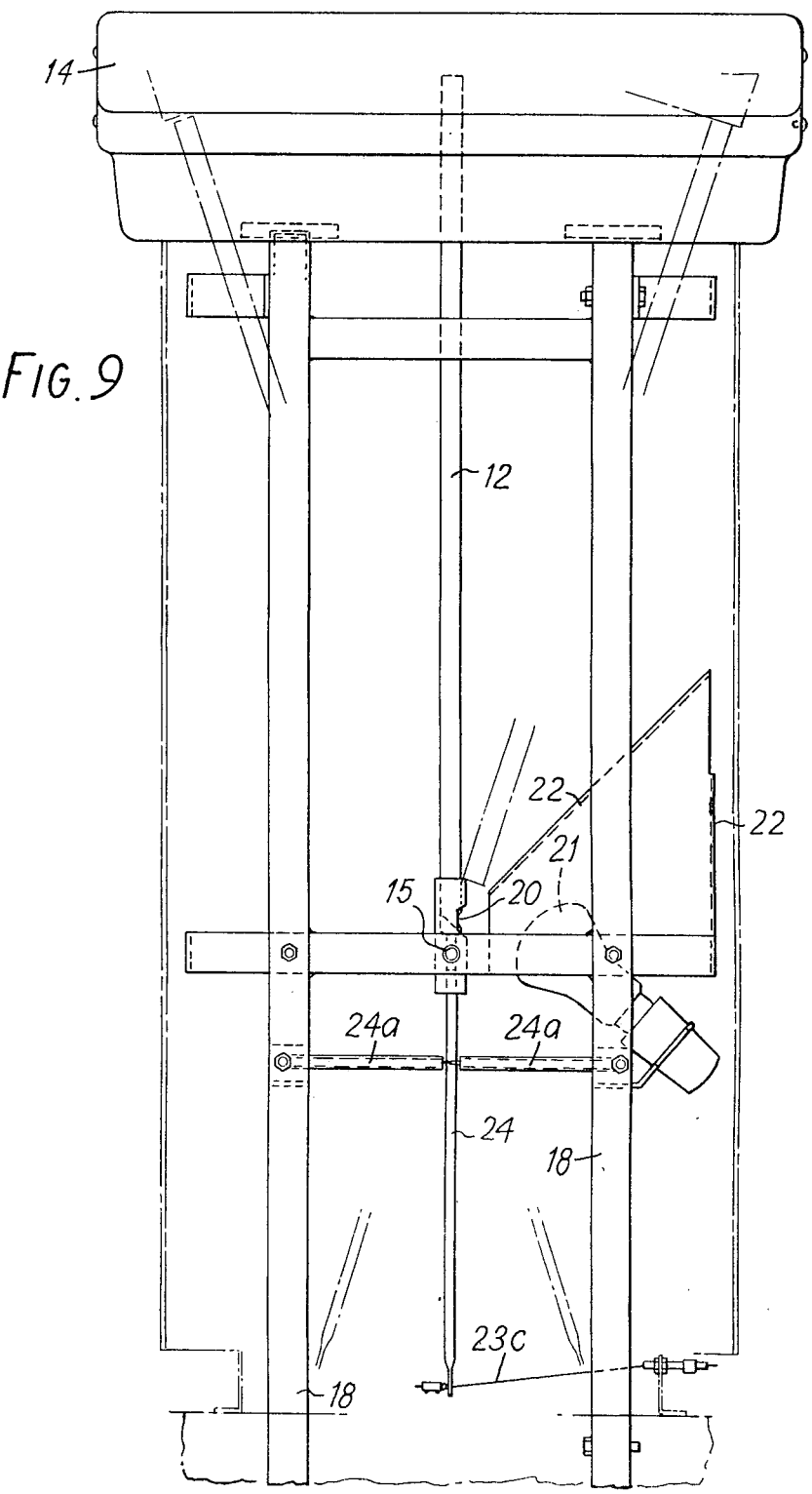

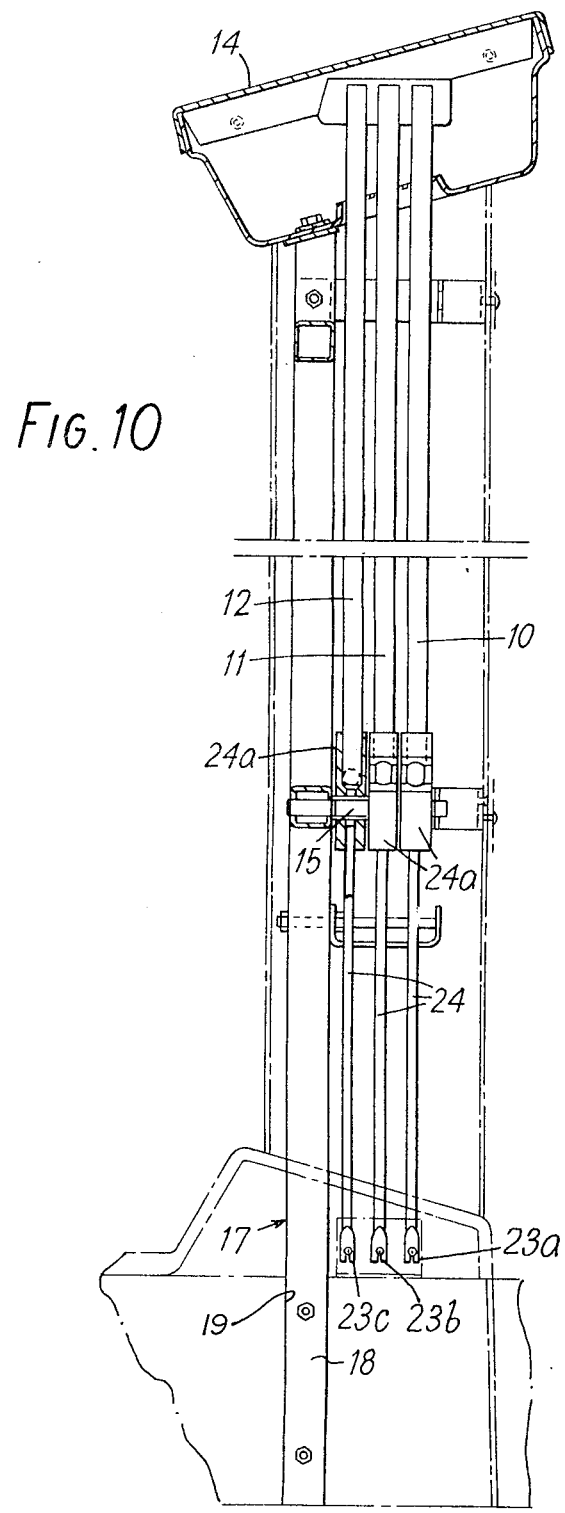

FOOT MEASURING MACHINES

This invention relates to foot measuring machines.

According to this invention there is provided a foot measuring machine comprising a platform for supporting a foot, a heel stop and a toe stop for respectively engaging the heel and toe of the foot, which stops are spaced apart lengthwise of the platform, a main carriage mounted for guided movement lengthwise of the platform, width probes mounted on the carriage for guided movement to engage opposite sides of the foot, means for moving the heel stop, toe stop and carriage relative to each other in a direction lengthwise of the platform and maintaining the distance between the width probes and the heel stop at substantially three-quarters of the distance between the toe stop and the heel stop, means for moving the width probes into engagement with opposite sides of the foot, and measuring means providing a measure of the distance travelled by the probes in moving from an initial position into a position in engagement with opposite sides of the foot thereby to provide a measure of the width of the foot. In one embodiment of the invention, the heel stop is fixed and the moving means drives the toe stop and the carriage lengthwise of the platform.

According to a preferred feature of the invention, the two width probes are mounted for lateral floating movement as a unit with respect to the carriage.

According to another preferred feature of the invention the width probes are mounted on respective trolleys on the carriage, said trolleys being mounted for guided movement transversely of the length of the foot relative to the carriage and carrying cam followers for engagement with cam means extending lengthwise of the platform, and means being provided for urging the trolleys in a sense to hold the cam followers in engagement with the cam means, said cam means being adapted to vary the distance between the trolleys as a function of the distance between the heel and toe stops thereby to provide a datum width, and to establish the initial positions of the width probes.

According to still another preferred feature of the invention the cam means is mounted for free lateral pivotal movement about one of its ends so as to provide said floating movement.

According to another preferred feature of the invention the carriage carries means for providing a measure of the girth of the foot at the position where the width of the foot is measured.

In preferred arrangements means is provided for establishing a datum girth at the position of measurement as a function of the measured width of the foot at that position, the girth measuring means providing a measure of the difference between the datum girth and the actual girth of the foot. In one such construction the girth measuring means comprises at each side of the platform a tape or band extending in a loop directed transversely to the lengthwise dimension of the platform and having its ends attached to the main carriage, a girth carriage mounted on the main carriage and having thereon two guide elements spaced apart transversely of the lengthwise dimension of the platform and engaged in the loop, and means for moving the girth carriages towards and away from each other, the construction and arrangement being such that inward movement of the carriage causes the guide elements to move within the loops the two inner guide elements being adapted to roll towards each other across the instep of a foot on the platform, and means for moving the carriages a predetermined distance inwards towards each other for bringing the inner guide elements into an initial relative position. Preferably the inner guide elements are resiliently urged towards each other so as to place the respective loops under tension, and one end of one of the loops is connected to a motor driven element operating in a sense to reduce the tension in the loop whereby the associated guide element is permitted to move forward to contact the inner guide element on the other carriage, there being provided switch means adapted to be actuated by a fall in the tension of said one of the loops to terminate movement of said motor driven element, which movement provides a measure of the girth of the foot.

The invention also provides a foot measuring machine comprising a platform for supporting a foot, a heel stop and a toe stop for respectively engaging the heel and toe of the foot, which stops are spaced apart lengthwise of the platform, a main carriage mounted for guided movement lengthwise of the platform, means for moving the heel stop, toe stop and carriage relative to each other in a direction lengthwise of the platform and maintaining the distance between the carriage and the heel stop at substantially three-quarters of the distance between the heel and toe stops, and means on the carriage for laying tape or other flexible band across the instep of the foot and for indicating a measure of the length of tape so laid thereby to provide a measure of the girth of the foot at the position of measurement.

The invention further provides a foot measuring machine comprising a platform for supporting a foot, a heel stop and a toe stop for respectively engaging the heel and toe of the foot which stops are spaced apart lengthwise of the platform, a main carriage mounted for guided movement lengthwise of the platform, means for moving the toe stop and the carriage simultaneously lengthwise of the platform and means on the carriage for laying tape or other flexible band across the instep of the foot and for indicating a measure of the length of tape so laid thereby to provide a measure of the girth of the foot at the position of measurement.

One embodiment of the invention will now be described by way of example with reference to the accompanying drawings in which:

FIG. 7 is a diagrammatic plan view of a girth carriage of the machine,

FIG. 8 shows diagrammatically the arrangement for providing the girth measurement reading, FIG. 9 is a front elevation of the pointer assembly of the machine with the external casing removed, and FIG. 10 is a sectional side elevation of the pointer assembly.

The illustrated machine is designed to measure the length of a person's foot and to measure the width and girth of the foot at a position 72.5% of the measured length of the foot from its heel end, which investigation has shown to be position of maximum width and maximum girth for most people. The machine establishes a datum girth for the foot on the basis of the measured width of the foot and then goes on to measure the variation from that datum girth. The machine indicates by means of a pointer 10 the most appropriate size-length of shoe for the foot based on its measured length, and indicates by means of a pointer 11 the most appropriate width fitting derived from the measured deviation from a datum width which is based on the typical maximum width of a foot of given length, and indicates by means of a pointer 12 whether the girth of the foot at the point of measurement of the width is low, normal or high. The datum width for each length of foot is greater than the maximum width likely to be encountered. In measuring the girth, the machine measures the variations of the girth from a datum which is less than the smallest girth likely to be met in a foot of given length.

Figure 1:
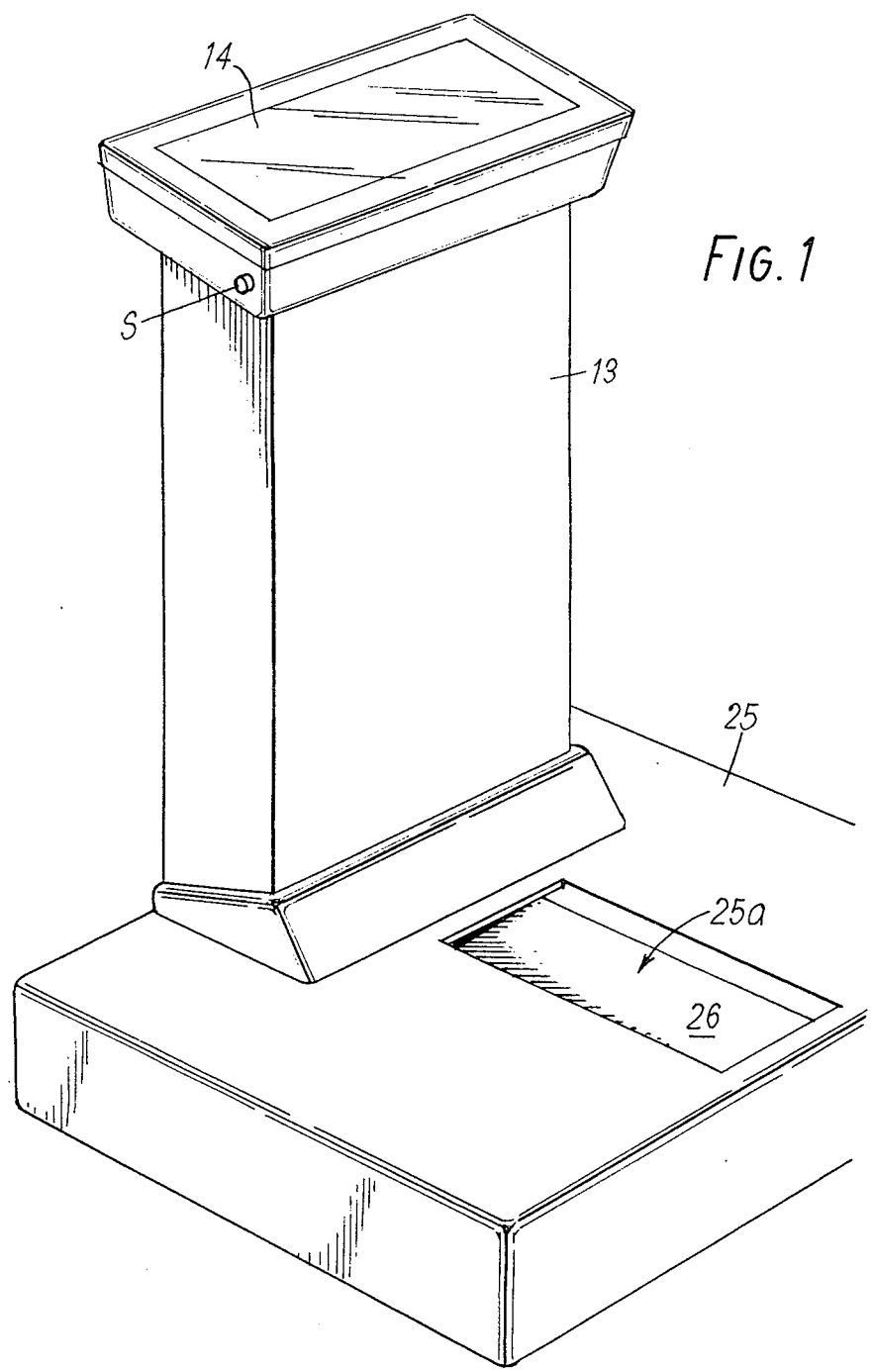
FIG. 1 is a perspective front view of a machine according to the invention.

Referring now to FIGS. 1, 9 and 10 the pointers 10, 11 and 12 and their respective scales are disposed in an upstanding indicator head 13 at the rear end of the machine. The size-length, width and girth fitting scales are marked side by side on a translucent screen 14. Pointers 10, 11 and 12 comprise transparent Perspex rods which are secured by one end in bosses 24a attached to respective lower lever portions 24. The bosses are mounted on a horizontal pivot pin 15 carried by a vertical frame 17, two uprights 18 of which have their lower ends secured in slots 19 near the rearward end of the chassis 16 of the machine. Each lever portion 24 is urged into a central position by opposed tension springs 24a acting on it. However, in the case of the lever portion of rod 10, the left hand tension spring, viewed as in FIG. 7 is a constant tension spring. The transparent Perspex rods are each notched at 20 near the pivot 15. An electric light bulb 21 partly enclosed by a casing structure 22 is directed on to the notches and light therefrom passes along each rod and is projected on to the screen 14 to indicate the scale reading. The length, width and girth dimensions measured by the machine are transmitted to the pointers by respective Bowden cables 23a, 23b, 23c connected to the lower ends of the lever portions. The range of swinging movement of the pointers is shown in chain lines in FIG. 10.

A casing 25 for the bottom part of the machine provides in its top face an elongate rectangular aperture 25a to receive a person's foot. The aperture is longer and wider than the largest foot the machine can measure. Below the aperture is disposed a horizontal platform 26 (FIGS. 1, 2 and 3) which is fixedly mounted at its ends on brackets forming part of a main chassis of the machine. A heel plate 28 is pivotally attached by its lower end to the upper surface of the platform 26 at the forward end of the latter. A microswitch 29 is disposed behind the heel plate 28 and when a foot to be measured is placed on the platform with the heel in engagement with the heel plate 28 to close the microswitch and a main switch S on the indicator head 13 has been actuated by the attendant to start an electric motor 30 mounted on the chassis 19 near the rear end of the machine.

Motor 30 drives, through a reduction gear train 31, a shaft 32 carried in bearings on the machine chassis. Shaft 32 extends across substantially the full width of the machine and has secured to each end a chain sprocket 33 and a wheel 34 which has a peripheral flange. Each of the wheels 34 has secured to its flange by a screw 34a one end of a constant tension spring 35 of the type known as Tensator springs, the other end of which is attached to a pulley 36 carried in bearings in the chassis adjacent the front end of the machine. A transversely extending bar 37 has its opposite ends secured to the two springs 35 respectively and supports a bracket 38 for movement lengthwise of platform 26. The bracket in turn carries for pivotal movement about a horizontal axis a toe-plate 39 behind which a microswitch 39a is attached to the bracket 38. The two springs 35 are designed to pull the bar 37 towards the heel plate with a constant tension of approximately one pound each. When motor 30 is started, the wheels 34 are driven to permit the Tensator springs to be drawn on to the pulleys 36, and when the toe plate 39 comes into abutment with the toes of the foot on the platform 26, a maximum pressure of two pounds is exerted by springs 35 but the constant tension spring acting on the lever portion 24 of rod 10 as previously described reduces the load applied to the toes to about ½ to 1 lb.

The toe plate swivels under this load and operates the microswitch 39a to stop the motor 30.

The other end of the Bowden cable 23a attached to the length pointer 10 is attached to bracket 38 and its cover is engaged in a holder (not shown) mounted on the rearward end of the platform so that the pointer 10 moves as bracket 38 moves and indicates the measured length of the foot.

Figure 2:
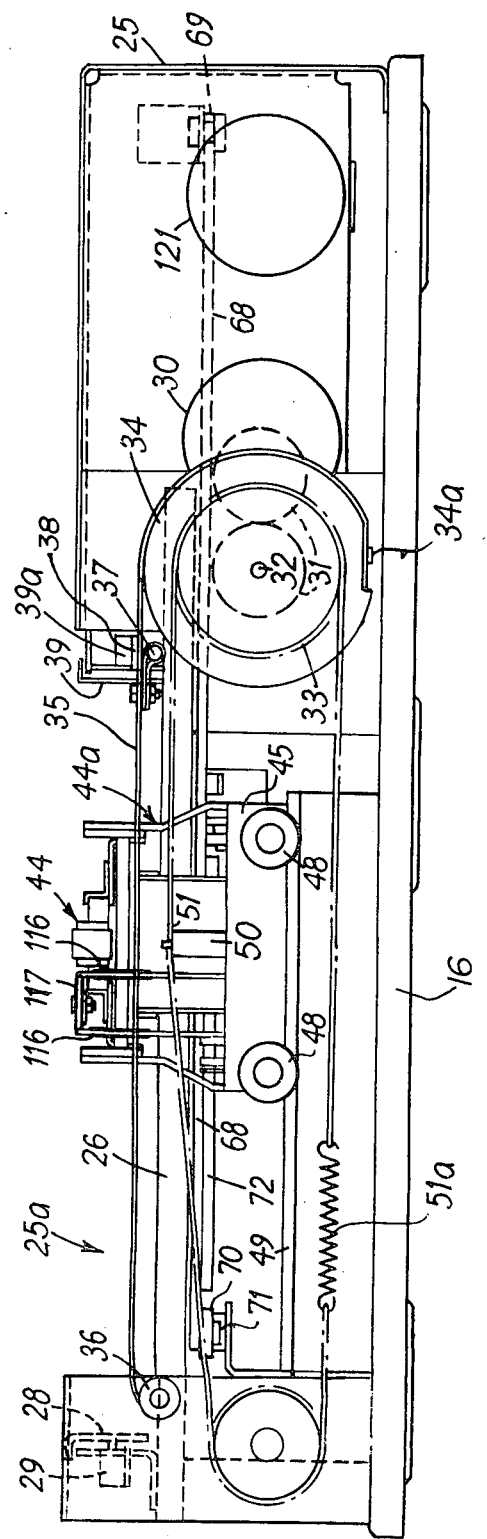
FIG. 2 is a side elevation of the machine, parts of the external casing being omitted to show the construction more clearly.

The width of the foot is measured by two width probes 40, 41 carried by respective trolleys 42, 43 which are mounted on a frame 44a forming part of a main carriage 44 spanning the chassis 16. Carriage 44 comprises a pair of side plates 45 interconnected by a rod 46 and a parallel channel section member 47 and carrying rollers 48 enabling the carriage to roll backwards and forwards along lengthwise extending rails 49 secured to the chassis 16 (FIG. 2). A post 50 projecting upward on each side plate 45 is connected to a link of a chain 51 extending round the sprocket 33 which is secured to the motor driven shaft 32 and round an idler sprocket 53 mounted on a stub shaft carried by the chassis 16 adjacent the pulley 35. The ends of the chain are interconnected by a tension spring 51a (FIG. 2).

As mentioned above it has been found by extensive investigations that on average the maximum width of the foot occurs at a distance equal to 72.5% of the length of the foot measured from the heel. The required ratio between the movement of the toe plate and the carriage 44 to ensure that the width sensors are at a distance from the heel plate equal to 72.5% of the distance of the toe plate from the heel plate is determined by the relationship between the effective diameters of the sprockets 33 and the wheels 34 which control the position of the toe plate 39.

Figure 6:
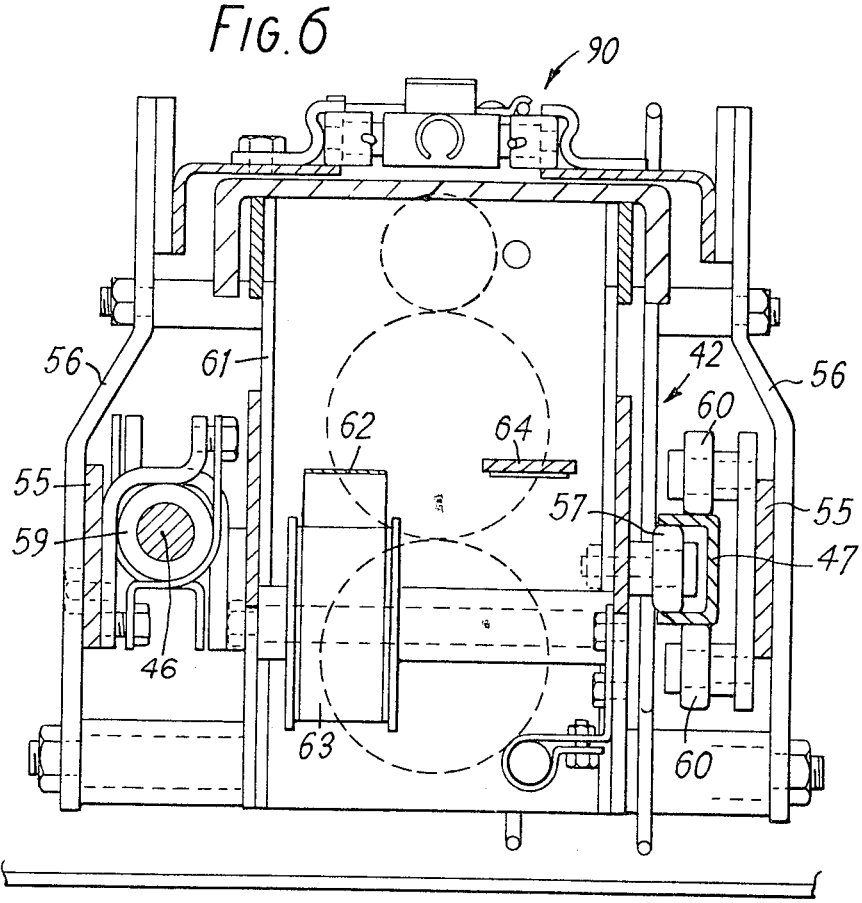
FIG. 6 is a sectional view on the plane 6—6 of FIG. 4.

The frame 44a which forms part of the carriage is rigid and has two vertical side parts disposed on opposite sides of the trolleys and extending parallel to and adjacent the rod 46 and member 47 respectively, these side parts being interconnected by horizontal rods 54. Each side part comprises a horizontal member 55 extending under the platform 26 with first uprights 56 at its ends, second uprights (which are not shown) spaced inwards from its ends and disposed adjacent opposite sides of the platform, and short horizontal members 58 interconnecting the upper ends of the first and second uprights at each side of the platform. The carriage frame 44a also has bearing sleeves 59 (FIG. 6) clamped thereto and encircling the rod 46 and rollers 60 engaging the top and bottom flanges of the channel section member 47, so that the frame can move laterally along the rod 46 and member 47. Each of the two trolleys comprises a box structure 61 which is supported between the side parts of the carriage frame 44a by bearing sleeves (not shown) clamped to the box structure behind the bearing sleeves 59 engaging the rod 46 and by rollers 57 engaging within the channel section member 47 enabling the trolleys to move relative to the carriage frame. The two trolleys are pulled towards each other by twin constant tension springs 62 each extending between a drum 63 on one trolley and an anchorage 64 on the other trolley but are held apart at a distance related to the measured length of the foot by a floating cam device which will now be described.

Referring now to FIGS. 2, 3, 4A and 4B two parallel links 68 extend along under the platform 26 and are pivotally attached to the chassis at 69 at their rearward ends, the front ends of the links being pivotally coupled together by a transverse link 70 which is supported beneath the platform by a block 71 made from polytetrafluoroethylene. Two generally triangular width cams 72 are respectively secured to the links 68 and each has outwardly facing contiguous cam edges 73, 74. The transverse distance between the two cam edges 73 or the two cam edges 74 at any point lengthwise of the cams represents the datum width for a corresponding foot length, and it is the variations from this datum width which are transmitted to the width pointer 15. The cam edges 73 represent the widths corresponding to children's shoe sizes and the cam edges 74 represent those corresponding to adult sizes. The cam edges 73, 74 of the two cams 72 are engaged by roller followers 75 (FIG. 4) adjustably mounted on the trolleys 42, 43. The inner edges of the cams are respectively engaged by rollers 76 adjustably mounted on the carrier frame 44a. The trolleys are pulled towards each other to maintain the rollers 75 in contact with the cams by the twin constant tension springs 62 which provides a constant pulling force of 2 lb. between the trolleys. The pivotal attachment of the links 68 to the machine chassis provides the assembly of the trolleys 42, 43 and width cams 72 with a transverse floating action without the occurrence of any appreciable error in the transverse datum distance between the rollers 75. The engagement of rollers 76 with the inner edges of the cams maintains the carriage 44a in a central position with respect to the two trolleys.

To bring the width probes 40, 41 into abutment with the sides of the foot, a gear train 80 mounted on trolley 43 is driven by a flexible cable drive (not shown) from an electric motor 81 mounted at the rearward end of the chassis and drives a gear wheel 82 which has a screw 83 secured to it. The screw has a standard and a non-standard thread in its length. The standard screw thread is engaged by a threaded sleeve 84 which is held against rotation and which is attached to an assembly 85 slidably mounted on the trolley and carrying the width probe 41. The width probe 41 is thus movable inwards towards and outwards away from width probe 40. In operation of the machine, the microswitch 39a operated by the toe plate 39 starts the motor 81 at the same time as it stops the motor 30, and motor 81 drives the gear train 80 in a sense to move the width probe 41 towards the side of the foot. When probe 41 touches the side of the foot, the continuing operation of motor 81 and probe 41 and the lateral floating action introduced by the mounting of the width cams together cause the trolleys 42, 43 to move transversely of the foot along the rod 46 and member 47 until the width probe 40 comes into abutment with the other side of the foot. A plate 85 (FIG. 5) on the inner end of each probe is mounted for a small degree of lost motion in the direction of movement of the probe. A small spring 86 holds each plate 85 at the inner extremity of its lost motion but is overcome when the probes press against opposite sides of the foot, and the resulting movement of the plates 85 relative to respective probes actuates microswitches 40a on the bodies of respective probes to stop the motor 81. Microswitches 40a are connected in series with each other. Springs 86 (see FIG. 5) are selected bearing in mind that the width probes can never exert a force greater than 2 lb. on the foot, i.e. a force equal to the total tension exerted by the constant tension springs 62. One of the gears in the gear train 80 driven by motor 81 has a drum 88 secured to it, and the end of the Bowden cable 23b remote from the pointer arrangement is attached to the drum, the end of the cable cover being held by a holder (not shown) on the box structure 61 of trolley 43. Thus the rotational movement of the drum 88 from its initial datum position is directly related to the movement of the threaded sleeve 84 along the screw thread necessary to bring the two probes 40, 41 into engagement with the sides of the foot, and this movement is transmitted by the Bowden cable to the pointer 11, indicating the variation from the standard width determined by the spacing between the two cam followers 72 and thus the required width fitting of the shoe.

Figure 3:
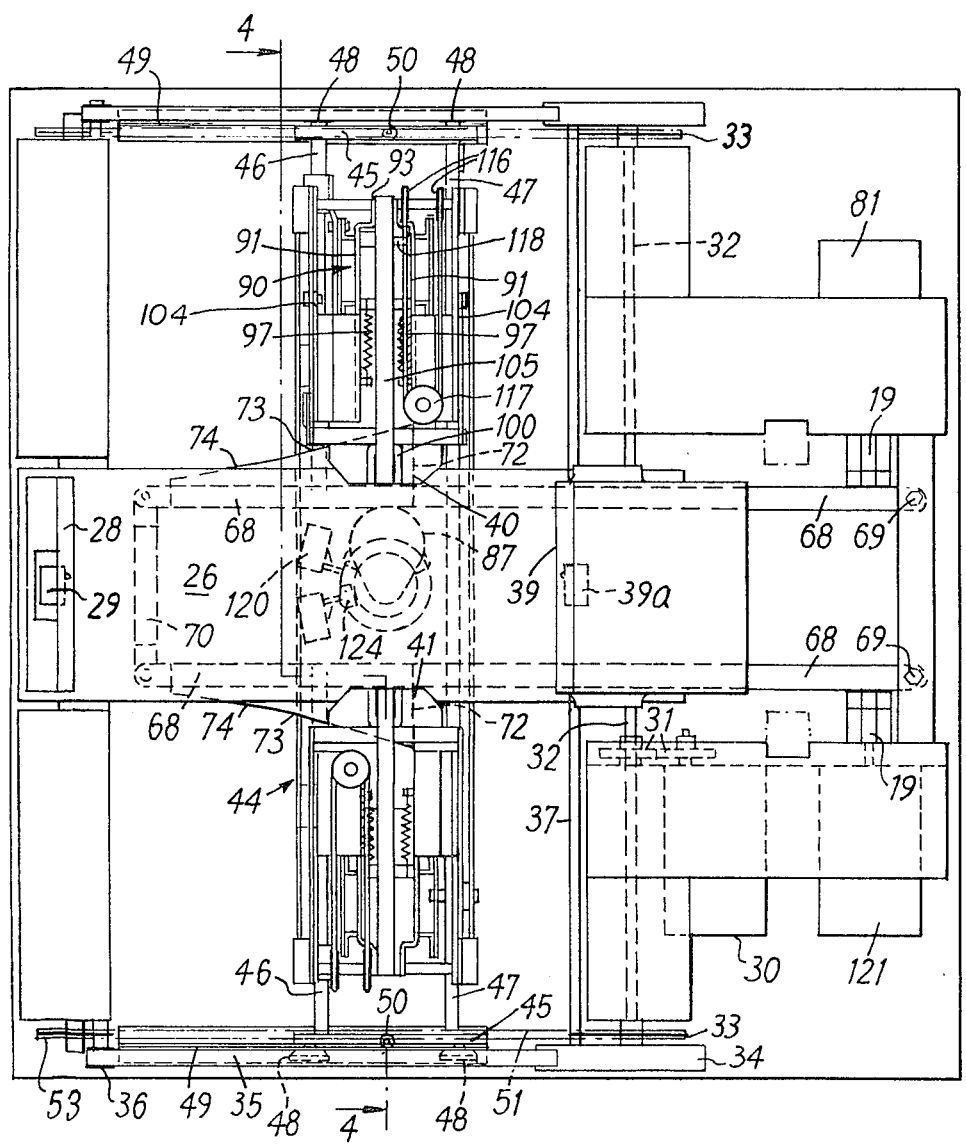
FIG. 3 is a plan view of the apparatus, the external casing being omitted to show the construction, FIGS. 4A and 4B together show an end elevation of the apparatus, FIG. 4B being partly sectioned on the plane 4—4 of FIG. 3
Figure 4B:
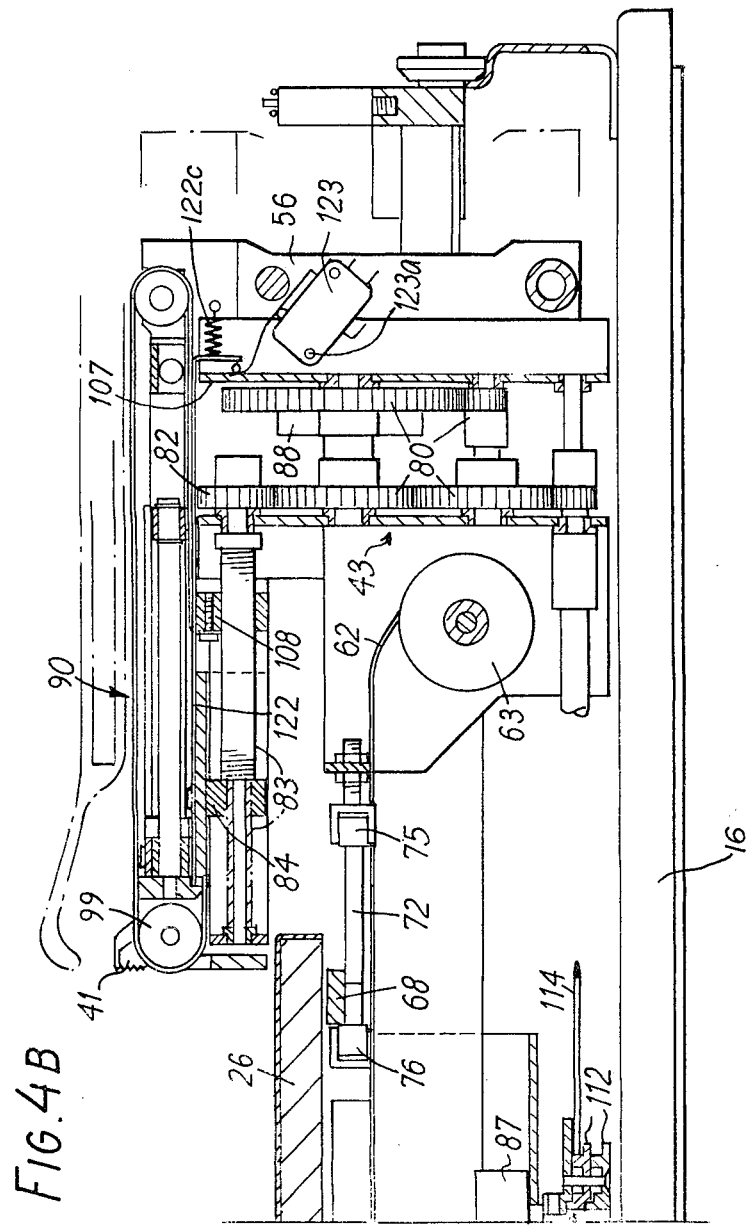

Each of the trolleys 42, 43 also carries a girth carriage 90 (FIGS. 4 and 7) comprising two side strips 91 which are secured together and which are slidably mounted on the top of the carriage frame for movement at right angles to the lengthwise dimension of platform 26. At its outer end (i.e., its end further from the platform 26) each carriage provides a transverse axle pin for a roller 93 as shown in FIGS. 7 and 8. A block 94 disposed between the side strips 91 has lateral pins 95 which project into slots 96 extending lengthwise of the side strips 91 and which respectively provide anchorages for two tension springs 97, the other ends of which are attached to inwardly directed pegs 98 fixed on the side strips 91. A second roller 99 is mounted inwardly of the inner ends of the side strips 91 in a yoke 100 which is rotatably mounted on a rod 101. Rod 101 extends outwards between the strips 91 and has its outer end mounted in the block 94. The mounting of the yoke 100 enables the roller 99 to tilt about the axis of rod 101. Between block 94 and the yoke, the rod 101 is rotatably mounted in a second block 102 which is carried by strips 103 extending laterally over the side strips 91 and secured at their outer ends to outwardly extending radius arms 104 pivotally mounted on the trolley 42 or 43 (FIG. 3). The rod 101 and roller 99 can thus also pivot upwards and downwards about the lateral pins 95 and are stabilised by block 102 and the radius arms 104. A tape 105 extends round the rollers 93 and 99.

A plate 122 (FIGS. 7 and 8) underlies the girth carriage and is slidably supported by carriage frame 44a for movement parallel to that of the girth carriage. The outer end of plate 122 has a vertical tail piece 122a (see FIG. 8) which is arranged to actuate a microswitch 123 and to which is connected one end of a weak tension spring 122c, the spring being anchored to carriage frame 44a and tending to pull the plate in an outward direction. The plate 122 is held against the spring tension by one end of the tape 105 which is attached to the inner end of the plate at 122b and extends thence forwardly (inwardly), upwardly round the inner roller 99, rearwardly, downwardly round roller 93 and then forwardly to an anchorage point. This anchorage point is not the same on the two trolleys 42, 43, as will now be explained. A plate 122 forms a first anchorage for each tape 105, the other anchorages of the right and left tapes being formed by the block 108 and the sleeve 126 respectfully.

On the right hand girth trolley at the right hand end of carriage frame 44a as viewed from the front of the machine, the said anchorage point is a block 108 (FIG. 4B) which is in engagement with the non-standard screw thread of screw 83. When the width probes 40, 41 move inward to measure the deviation of the width of the foot from the corresponding datum width for the length of the foot, the starting position of block 108 and said other end of the girth measuring tape on the right hand trolley is automatically adjusted to set the girth datum corresponding to the measured width of the foot. This adjustment thus moves the said other end of tape 105 (FIGS. 7 and 8) which in turn adjusts the position of the inner roller 99 relative to the girth carriage the lateral pins 95 moving along their slots 96 to compensate.

A motor 87 (FIGS. 4A and 4B) which is disposed below platform 26 and which is started by the microswitch 39a actuated by the toe plate 39 has two pulleys 112 on its output shaft, and the pulleys drive endless cords 113, 114 extending round pulley systems associated with the respective trolleys 42, 43 and mounted on the carriage frame. Each of these pulley systems comprises pairs of pulleys 115 and 116 (FIGS. 3 and 4A) carried on rods 54 and a pulley 117 mounted on a vertical pin carried by the carriage frame. A clip 118 (FIG. 3) on the run of each endless cord between one pulley 116 and pulley 117 is connected to the associated girth frame 90, so that when the motor 87 is set in forward operation from its predetermined starting position the two girth frames are moved towards each other from their predetermined initial positions. A first microswitch 120 associated with motor 87 is provided for stopping the motor and simultaneously starting a motor 121 mounted adjacent the rear end of the chassis. Since each girth carriage is thus effectively moved inward a predetermined distance, the position of the inner roller 99 of the right hand girth carriage continues to be indicative of the girth datum. It will be understood that since the ends of the tapes are not attached to the girth carriage the rollers 93, 99 roll within the loop of tape during the forward movement of each girth carriage.

On the girth carriage 90 on the left hand end of the carriage frame 44a, the said anchorage point to which the end of the tape 105 is connected is a threaded sleeve 126 (FIGS. 5 and 8) mounted on a screwed rod 127 which is supported in bearings on carriage frame 44a. Sleeve 126 has a lateral extension 126a slidably engaged with a rod 129 carried by trolley 42 so as to hold the sleeve against rotation. Screwed rod 127 is driven by a motor 121 (FIG. 3) at the rear end of the chassis through a flexible cable (not shown) and a gear train (not shown) carried by the carriage frame 44a. One of the gears in the train has a drum secured to it in the same manner as in the gear train 80 (FIG. 4B), and the end of the Bowden cable 23c remote from the pointer system is attached to and wound on the drum.

Each of the plates 122 (FIGS. 8 and 4B) is positively restrained against forward movement beyond a point at which a selected tension is applied to its spring 122c. In the illustrated construction this is achieved by abutment of the vertical tail pieces 122a of the plates against the outer ends 107 of the respective gear boxes housing the gear trains driven by motors 81 and 121.

When forward motion of the motor 87 beneath platform 26 (FIGS. 4A and 4B) is initiated by microswitch 39a the two girth carriages are moved bodily inward by the endless cords 113, 114 in the manner described above at a speed which is substantially the same as the speed of movement of the width probes 40, 41. During this movement of the girth carriages, the two ends of each tape 105 (FIGS. 7 and 8) being effectively fixed, the rollers 93 and 99 roll within the tapes. The motor 87 remains in operation after the width probes have stopped and carries the girth probes constituted by the rollers 99 inward towards each other across the foot. The rollers roll across the instep of the foot and can lift and tilt by virtue of their mountings 102, 104 on the girth frames to keep in proper rolling contact with the foot. The motor 87 is stopped by the operation of a microswitch 120 (FIG. 3), at a selected rotational position of its pulleys 112, by a projection 124 attached to one of the pulleys, when the girth probes, rollers 99, are still a short distance apart.

Figure 5:
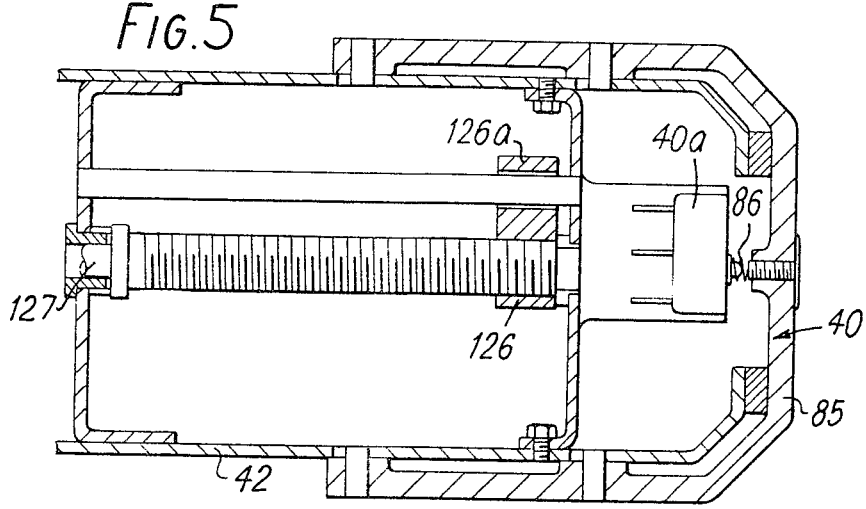
FIG. 5 is a fragmentary sectional plan on the plane 5—5 of FIG. 4.

The actuation of microswitch 120 also initiates operation of motor 121 to drive the screwed rod 127 in a sense to move the threaded sleeve 126 on the left hand girth carriage outwards (FIGS. 5 and 8). This allows the tape 105 on the carriage to be fed inward round the roller 93, which in turn allows the roller 99 to be moved inward by the tension springs 97 towards the roller 99 on the right hand girth carriage.

When the left hand roller 99 touches the stationary right hand roller 99, continued movement of the threaded sleeve 126 (FIG. 8) causes the tension in the tapes 105 of both girth carriages to fall and this reduction of tension is transmitted to the underlying plates 122 and allows the plates to be pulled outwards by their respective springs 122c to actuate the microswitches 123, to stop motor 121. The operation of motor 121 is terminated when both of the microswitches 123 have been actuated. The length of Bowden cable 23c which has been fed on to the drum on the left hand trolley 42 by the rotation of the motor 121 is a measure of the deviation of the actual girth of the foot from the datum value and serves to move the pointer 12 to provide an appropriate reading on the scale. The setting of each of the microswitches 123 can be adjusted by altering its rotational position about its fixing bolt 123a.

The sequence of events is thus briefly as follows. Placing of the foot on platform 26 with the heel against the heel plate 28 actuates microswitch 29 to start motor 30. Motor 30 drives wheels 34 and chain sprockets 33 to move the toe plate assembly towards the toe and simultaneously to move the carriage 44 to maintain its transverse centre line at a constant distance from the heel plate equal to 72.5% of the distance between the toe plate and heel plate. When the toe plate touches the toe of the foot, the microswitch 39a stops the motor and simultaneously starts the width probe motor 81 and the girth carriage motor 87. The movement of the toe plate has been transmitted by cable to pointer 10. The two trolleys 42, 43 have been moved towards each other by the constant tension springs 62 to the extent permitted by the floating cam mechanism beneath platform 26 to set the spacing between the trolleys, and hence the width datum, at a value related to the measured length of the foot. Movement of the width probes into engagement with the sides of the foot is actuated from the right hand trolley, the floating cam mechanism now operating to cause the left hand width probe 40 to be drawn into engagement with the side of the foot. The actuating movement of motor 81 is measured by the amount of cable drawn on to the drum 88 and is transmitted to the pointer 11 to provide a width fitting reading based on the deviation from the datum width for the measured length of the foot, the datum for each length of foot being wider than the widest foot likely to be encountered. Simultaneously with the operation of the width probes 40, 41 a datum correction related to the measured width of the foot is being applied by threaded block 108 to the right hand girth probe (roller 99), and inward movement of the girth probes is actuated by motor 87 through endless cords 113, 114. This inward movement continues after the width probes have stopped and brings the right hand girth probe to a datum position, and is terminated by stopping of motor 87 by microswitch 120, which simultaneously starts motor 121 to actuate a measured further inward movement of the right hand girth probe 99 which movement is transmitted to pointer 12.

When the scale readings have been noted, release of the press-button switch S initiates reversal of the motors of the mechanism to return the components to their starting positions.

In a modified arrangement, the drum 88 and its driving gear are respectively replaced by a rack and pinion the rack being slidably mounted on the trolley, and the cable being connected to the rack. The corresponding components on trolley 42 may be similarly replaced.

The illustrated arrangement determines the girth datum in part in dependence on the shape of the cams 68 of the floating cam arrangement, but these cams are designed primarily to set the width datum. To provide an improved initial girth datum setting, the illustrated arrangement may be modified by incorporating a second floating cam which is in the form of a long narrow substantially triangular plate having the apex which provides its smallest angle mounted for pivotal movement about a vertical axis in the region of the rearward end of the platform and substantially aligned with the path of movement of the anchorage 107 of the girth tape on the right hand trolley in the illustrated arrangement. However, in the modified arrangement the end of the tape is secured to a block and the width dimension of the cam is disposed between the block and a point on the trolley corresponding to the anchorage 107. The block is slidable relative to the trolley in a direction towards and away from the cam, and the block and the trolley carry follower rollers for respectively engaging opposite side edges of the cam. The block is spring-loaded towards the cam. Thus, as the trolley moves with the frame 44a during the measurement of the length of the foot, the floating cam adjusts the position of the end of the tape remote from the block 108 in dependence on the measured length of the foot. The floating cam has portions of its cam edge designed respectively for children's and adult's sizes similarly to the edges 73, 74 respectively of the width cams 72.

The right hand girth carriage may have a plate 122, microswitch 123 and spring 122c associated with it in the same manner as shown in FIGS. 7 and 8, and in that case the operation of motor 121 is terminated when both of the microswitches have been actuated by the relaxing of the tensions in the respective tapes.

I claim:

1. A foot measuring machine comprising a chassis, a platform for supporting a foot, said platform being mounted on the chassis, a heel stop and a toe stop for respectively engaging the heel and toe of the foot, said stops being spaced apart lengthwise of the platform, a main carriage mounted on the chassis for guided movement lengthwise of the platform, cam means extending lengthwise of the platform and providing laterally oppositely facing cam surfaces, said cam means being mounted on the chassis for free sideways movement with respect to the platform, trolleys mounted on the carriage at opposite sides of the platform for guided movement relative to the carriage in a direction at right angles to the lengthwise dimension of the platform for engaging opposite sides of the foot, cam followers secured to the respective trolleys and respectively engaging said cam surfaces, means connected to urge the trolleys resiliently towards each other, a pair of width probes each of which is mounted on a separate said trolley to engage opposite sides of the foot, one of said width probes being fixed on its respective trolley and the other of said width probes being mounted for guided movement relative to its trolley in a direction at right angles to the lengthwise dimension of the platform, means for relatively moving the heel stop, toe stop and carriage in a direction lengthwise of the platform and maintaining the distance between the width probes and the heel stop at substantially three-quarters of the distance between the toe stop and the heel stop, first measuring means providing a measure of the distance between the toe and heel stops thereby to provide a measure of the length of the foot, means for moving said other width probe relative to its trolley in a direction at right angles to the lengthwise dimension of the platform, and second measuring means providing a measure of the distance travelled by said other width probe relative to its trolley in moving from an initial position into a position in which the two width probes are in engagement with opposite sides of the foot thereby to provide a measure of the width of the foot.

2. A machine as claimed in claim 1, wherein the cam means is mounted for free lateral pivotal movement about one of its ends.

3. A machine as claimed in claim 1, wherein the carriage carries automatic means for providing a measure of the girth of the foot at the position where the width of the foot is measured.

4. A machine as claimed in claim 3, wherein means is provided for establishing a datum girth at the position of measurement as a function of the measured width of the foot at that position, the girth measuring means providing a measure of the difference between the datum girth and the actual girth of the foot.

5. A machine as claimed in claim 4, wherein the girth measuring means comprises at each side of the platform a tape or band extending in a loop directed transversely to the lengthwise dimension of the platform and having its ends attached to the main carriage, a girth carriage mounted on the main carriage and having thereon two guide elements spaced apart transversely of the lengthwise dimension of the platform and engaged in the loop, end means for moving the girth carriages towards and away from each other, the construction and arrangement being such that inward movement of the carriages causes the guide elements to move within the loops the two inner guide elements being adapted to roll towards each other across the instep of a foot on the platform, and means for moving the girth carriages a predetermined distance inwards towards each other for bringing the inner guide elements into an initial relative position.

6. A machine as claimed in claim 5, wherein the inner guide elements are each resiliently urged towards the other so as to place the respective loops under tension, and wherein one end of one of the loops is connected to a motor driven element operating in a sense to reduce the tension in the loop whereby the associated guide element is permitted to move forward to contact the inner guide element on the other carriage, there being provided switch means adapted to be actuated by a fall in the tension of said one of the loops to terminate movement of said motor driven element, which movement provides a measure of the girth of the foot.

7. A machine as claimed in claim 6, wherein means is provided for adjusting the effective length of one of the loops in dependence on the width of the foot as measured by the width probes.

8. A machine as claimed in claim 6, wherein means is provided for adjusting the effective length of one of the loops in dependence on the position of the carriage lengthwise of the platform.

9. A machine as claimed in claim 8, wherein the adjusting means comprises a cam plate extending generally parallel to the platform and disposed at one side of the platform, the widthwise dimension of said cam being resiliently gripped between a follower on the main carriage and a follower attached to one end of the adjustable loop.

10. A machine as claimed in claim 9, wherein the cam plate is mounted on a fixed part of the machine for lateral pivotal movement.

11. A machine as claimed in claim 19, wherein the heel stop is fixed and the moving means drives the toe stop and the carriage lengthwise of the platform.

12. A machine as claimed in claim 11, wherein the moving means comprises two wheels fixed to a common drive shaft and a driving band extending drivingly around each wheel to which driving bands the toe stop and carriage are respectively drivingly secured, the diameter of the wheel which drives the carriage being approximately three-quarters of the diameter of the wheel which drives the toe stop.

13. A machine as claimed in claim 12, wherein the driving band extending around the wheel which drives the toe stop is a constant tension spring urging the toe stop in a direction towards the heel.

14. A foot measuring machine comprising a platform for supporting a foot, a heel stop and a toe stop mounted above said platform for respectively engaging the heel and toe of the foot, which stops are spaced apart lengthwise of the platform, a main carriage mounted for guided movement lengthwise of the platform, means for moving the heel stop, toe stop and carriage relative to each other in a direction lengthwise of the platform and maintaining the distance between a point on the carriage and the heel stop at substantially three-quarters of the distance between the heel and toe stops, and at least one girth probe mounted on the carriage, first and second tape anchorages on the carriage, a flexible tape having its ends attached to said anchorages and extending in a direction normal to said lengthwise direction around the probe between said anchorages, means for moving the probe across the instep of a foot on the platform thereby to lay said tape across the instep of the foot and means for indicating a measure of the length of tape so laid thereby to provide a measure of the girth of the foot.

* * * * *